US011272953B2

(12) United States Patent
Boudreaux

(10) Patent No.: US 11,272,953 B2
(45) Date of Patent: Mar. 15, 2022

(54) ARTICULATION JOINT FOR SURGICAL INSTRUMENT

(71) Applicant: Ethicon LLC, Guaynabo, PR (US)

(72) Inventor: Chad P. Boudreaux, Cincinnati, OH (US)

(73) Assignee: Cilag GmbH International, Zug (CH)

(*) Notice: Subject to any disclaimer, the term of this patent is extended or adjusted under 35 U.S.C. 154(b) by 166 days.

(21) Appl. No.: 16/429,129

(22) Filed: Jun. 3, 2019

(65) Prior Publication Data
US 2019/0321070 A1 Oct. 24, 2019

Related U.S. Application Data

(63) Continuation of application No. 15/090,670, filed on Apr. 5, 2016, now Pat. No. 10,405,876.

(51) Int. Cl.
A61B 17/32 (2006.01)
A61B 17/3211 (2006.01)
(Continued)

(52) U.S. Cl.
CPC .. *A61B 17/320092* (2013.01); *A61B 17/3211* (2013.01); *A61B 17/320016* (2013.01);
(Continued)

(58) Field of Classification Search
CPC ....... A61B 117/32; A61B 17/00; A61B 17/29; A61B 17/320092; A61B 2017/00309;
(Continued)

(56) References Cited

U.S. PATENT DOCUMENTS 5,322,055 A 6/1994 Davison et al.
5,873,873 A 2/1999 Smith et al.
(Continued)

FOREIGN PATENT DOCUMENTS

CN 1907241 A 2/2007
CN 104042280 A 9/2014
(Continued)

OTHER PUBLICATIONS

European Communication dated Sep. 26, 2019 for Application No. 17718665.7, 5 pages.
(Continued)

*Primary Examiner* — George J Ulsh
(74) *Attorney, Agent, or Firm* — Frost Brown Todd LLC

(57) ABSTRACT

A surgical apparatus includes a body, an ultrasonic transducer, a shaft, an acoustic waveguide, an articulation section, an end effector, and a restricting member. The ultrasonic transducer is operable to convert electrical power into ultrasonic vibrations. The shaft couples the end effector and the body together. The acoustic waveguide is coupled with the transducer. The articulation section is operable to flex to thereby deflect the end effector from a longitudinal axis defined by the shaft. The restricting member is operable to restrict lateral deflection of the end effector. The restricting member is further operable to cooperate with a translating member to rigidize the articulation section when the end effector is aligned with the longitudinal axis. Such rigidization includes removing any "play" or other small movement that might otherwise be provided by the articulation section due to manufacturing tolerances and/or looseness between parts.

20 Claims, 13 Drawing Sheets

(51) Int. Cl.
*A61B 17/00* (2006.01)
*A61B 17/29* (2006.01)

(52) U.S. Cl.
CPC ............... *A61B 2017/00309* (2013.01); *A61B 2017/00314* (2013.01); *A61B 2017/00323* (2013.01); *A61B 2017/00327* (2013.01); *A61B 2017/2901* (2013.01); *A61B 2017/2905* (2013.01); *A61B 2017/2927* (2013.01); *A61B 2017/2929* (2013.01); *A61B 2017/320071* (2017.08); *A61B 2017/320094* (2017.08); *A61B 2017/320095* (2017.08)

(58) Field of Classification Search
CPC .. A61B 2017/00327; A61B 2017/2901; A61B 2017/2905; A61B 2017/2927; A61B 2017/2929; A61B 2017/320071; A61B 17/320016; A61B 17/3211
See application file for complete search history.

(56) References Cited

U.S. PATENT DOCUMENTS

| | | | |
|---|---|---|---|
| 5,897,523 A | 4/1999 | Wright et al. |
| 5,980,510 A | 11/1999 | Tsonton et al. |
| 5,989,264 A | 11/1999 | Wright |
| 6,063,098 A | 5/2000 | Houser et al. |
| 6,090,120 A | 7/2000 | Wright et al. |
| 6,325,811 B1 | 12/2001 | Messerly |
| 6,454,782 B1 | 9/2002 | Schwemberger |
| 6,589,200 B1 | 7/2003 | Schwemberger et al. |
| 6,752,815 B2 | 6/2004 | Beaupre |
| 6,773,444 B2 | 8/2004 | Messerly |
| 6,783,524 B2 | 8/2004 | Anderson et al. |
| 7,135,030 B2 | 11/2006 | Schwemberger et al. |
| 7,621,930 B2 | 11/2009 | Houser |
| 8,245,594 B2 | 8/2012 | Rogers et al. |
| 8,461,744 B2 | 6/2013 | Wiener et al. |
| 8,591,536 B2 | 11/2013 | Robertson |
| 8,623,027 B2 | 1/2014 | Price et al. |
| 8,663,220 B2 | 3/2014 | Wiener et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,339,271 B2 | 5/2016 | Ranucci et al. |
| 10,034,683 B2 | 7/2018 | Monroe et al. |
| 10,405,876 B2 | 9/2019 | Boudreaux |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0078247 A1 | 3/2012 | Worrell et al. |
| 2012/0112687 A1 | 5/2012 | Houser et al. |
| 2012/0116265 A1 | 5/2012 | Houser et al. |
| 2013/0289592 A1 | 10/2013 | Stulen et al. |
| 2014/0005701 A1 | 1/2014 | Olson et al. |
| 2014/0005703 A1 | 1/2014 | Stulen et al. |
| 2015/0080924 A1 | 3/2015 | Stulen et al. |
| 2015/0141981 A1 | 5/2015 | Price et al. |
| 2015/0320437 A1 | 11/2015 | Worrell et al. |

FOREIGN PATENT DOCUMENTS

| | | |
|---|---|---|
| CN | 105050514 A | 11/2015 |
| EP | 1 709 987 A1 | 10/2006 |
| JP | 2009-112795 A | 5/2009 |
| JP | 2012-527918 A | 11/2012 |
| JP | 2015-500046 A | 1/2015 |
| WO | WO 98/56299 A1 | 12/1998 |
| WO | WO 2012/114781 A | 8/2012 |
| WO | WO 2015/115196 A | 8/2015 |

OTHER PUBLICATIONS

International Search Report and Written Opinion dated Jul. 14, 2017 for International Application No. PCT/US2017/025958, 14 pages.
U.S. Appl. No. 14/258,179, filed Apr. 22, 2014.
U.S. Appl. No. 61/410,603, filed Nov. 5, 2010.
Chinese Office Action, The First Office Action and First Search, dated Nov. 3, 2020 for Application No. CN 201780030938.X, 7 pgs.
Chinese Office Action, Notification of Second Office Action, dated Jul. 5, 2021 for Application No. CN 201780030938.X, 11 pgs.
Japanese Office Action, Notification of Reasons for Refusal and Search Report by Registered Search Organization, dated Apr. 6, 2021 for Application No. JP 2018-552241, 23 pgs.
European Communication dated May 11, 2020 for Application No. EP 17718665.7, 5 pgs.

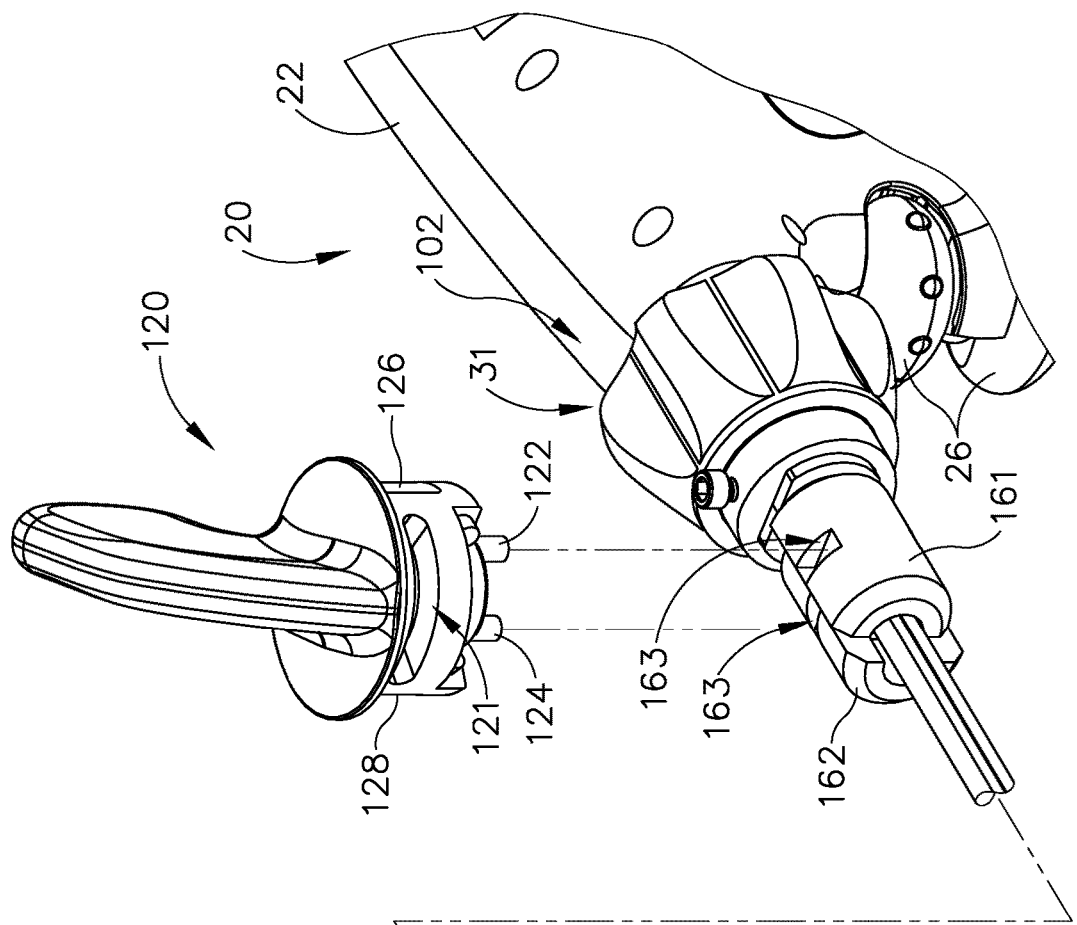
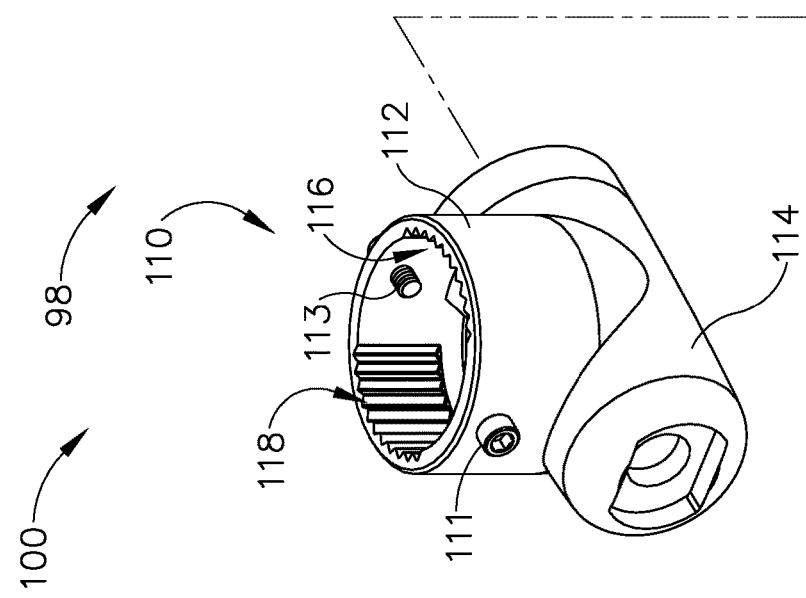
Fig. 9

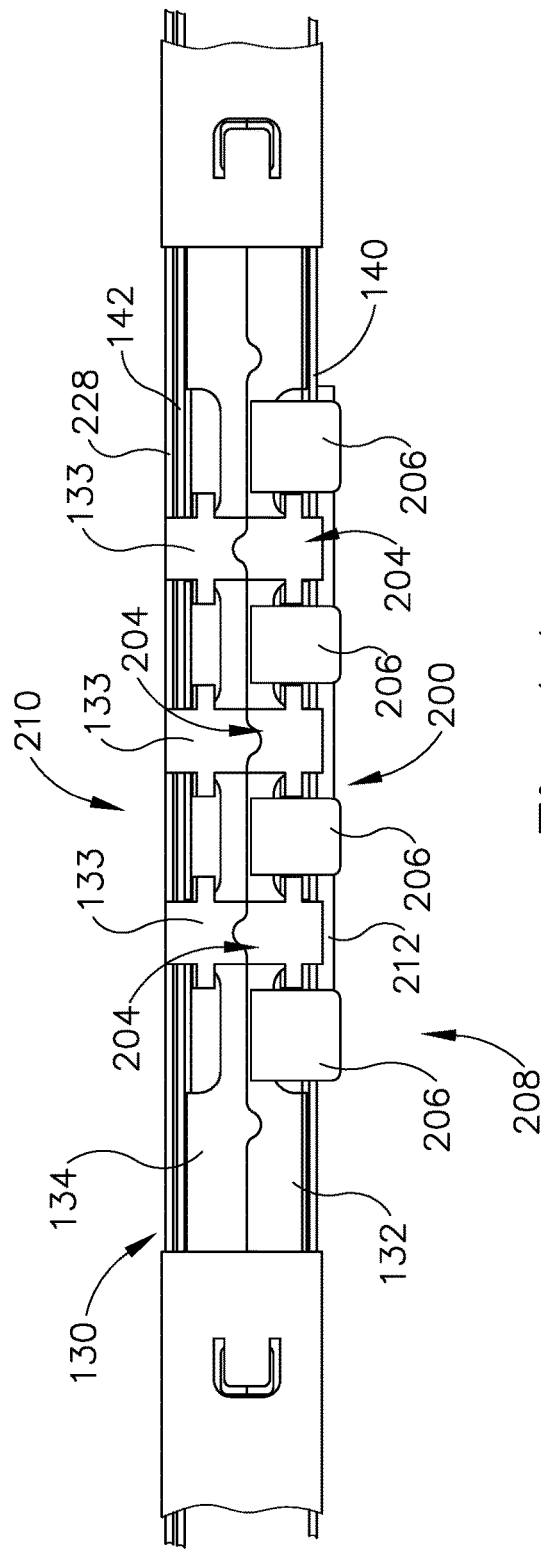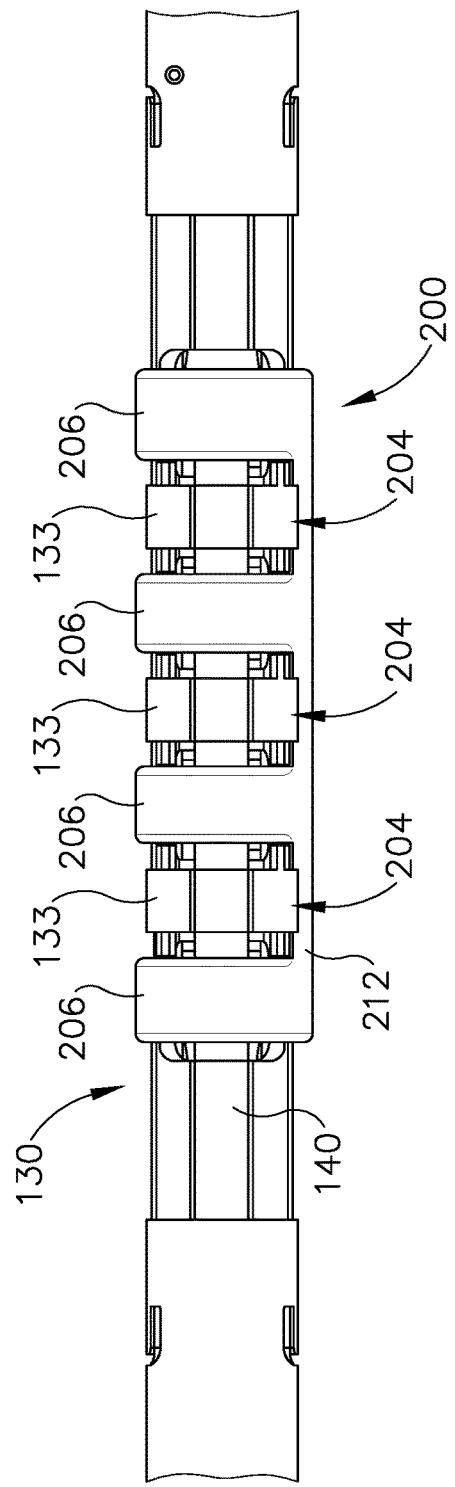

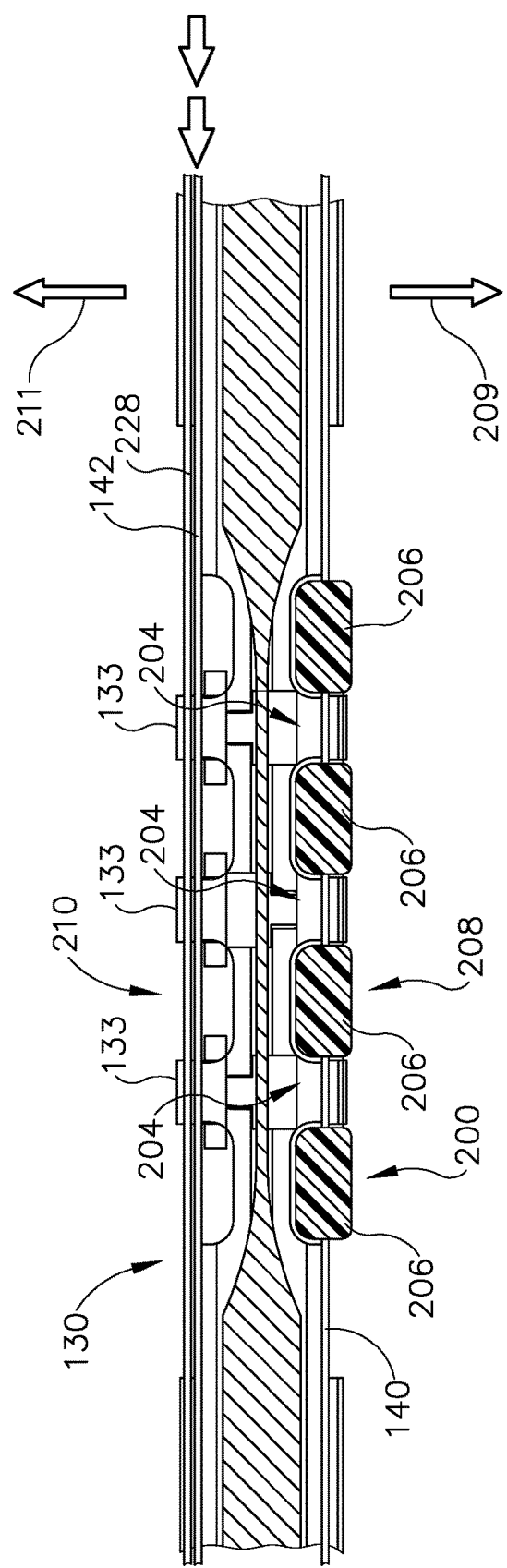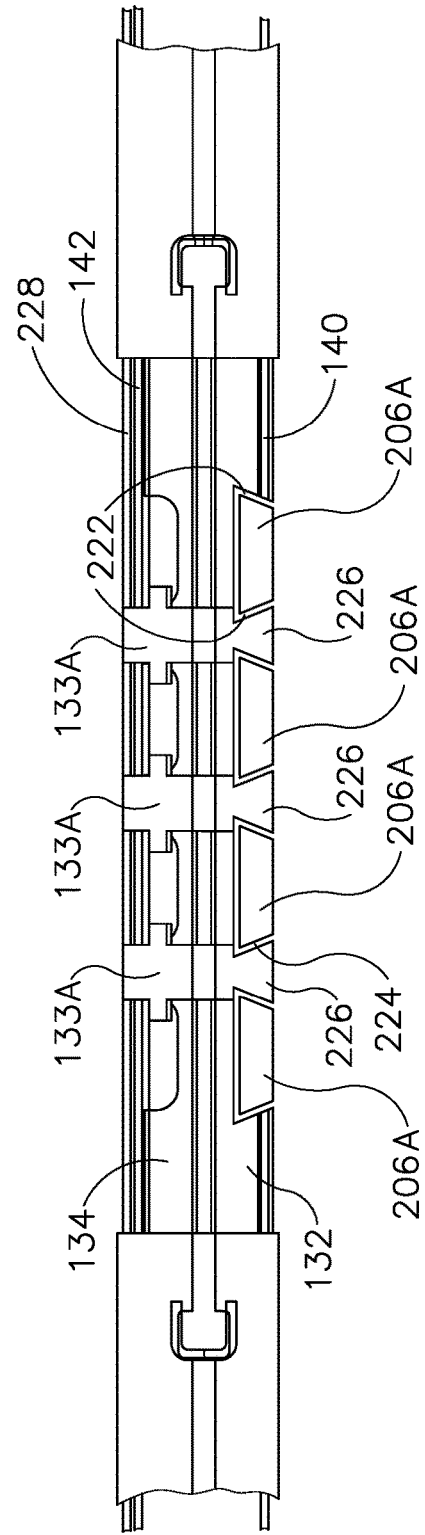

ARTICULATION JOINT FOR SURGICAL INSTRUMENT

This application is a continuation of U.S. patent application Ser. No. 15/090,670, entitled "Articulation Joint for Surgical Instrument," filed on Apr. 5, 2016, issued as U.S. Pat. No. 10,405,876 on Sep. 10, 2019, the entire disclosure of which is expressly incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, now 62/176,880 entitled Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9 depicts a partially exploded perspective view of an articulation control assembly of the instrument of FIG. 1;

FIG. 14 depicts a top plan view of the restricting member and articulation section of FIG. 12;

FIG. 15 depicts a side elevational view of the restricting member and articulation section of FIG. 12;

FIG. 16B depicts a cross-sectional top view of the restricting member and articulation section of FIG. 12 in a straight configuration; and FIG. 17 depicts a top plan view of an exemplary variation of the articulation section of FIG. 2, with an exemplary alternative restricting member having a set of wedge-shaped tabs disposed in corresponding complementary set of wedge-shaped spaces defined by the articulation section.

Figure 1:
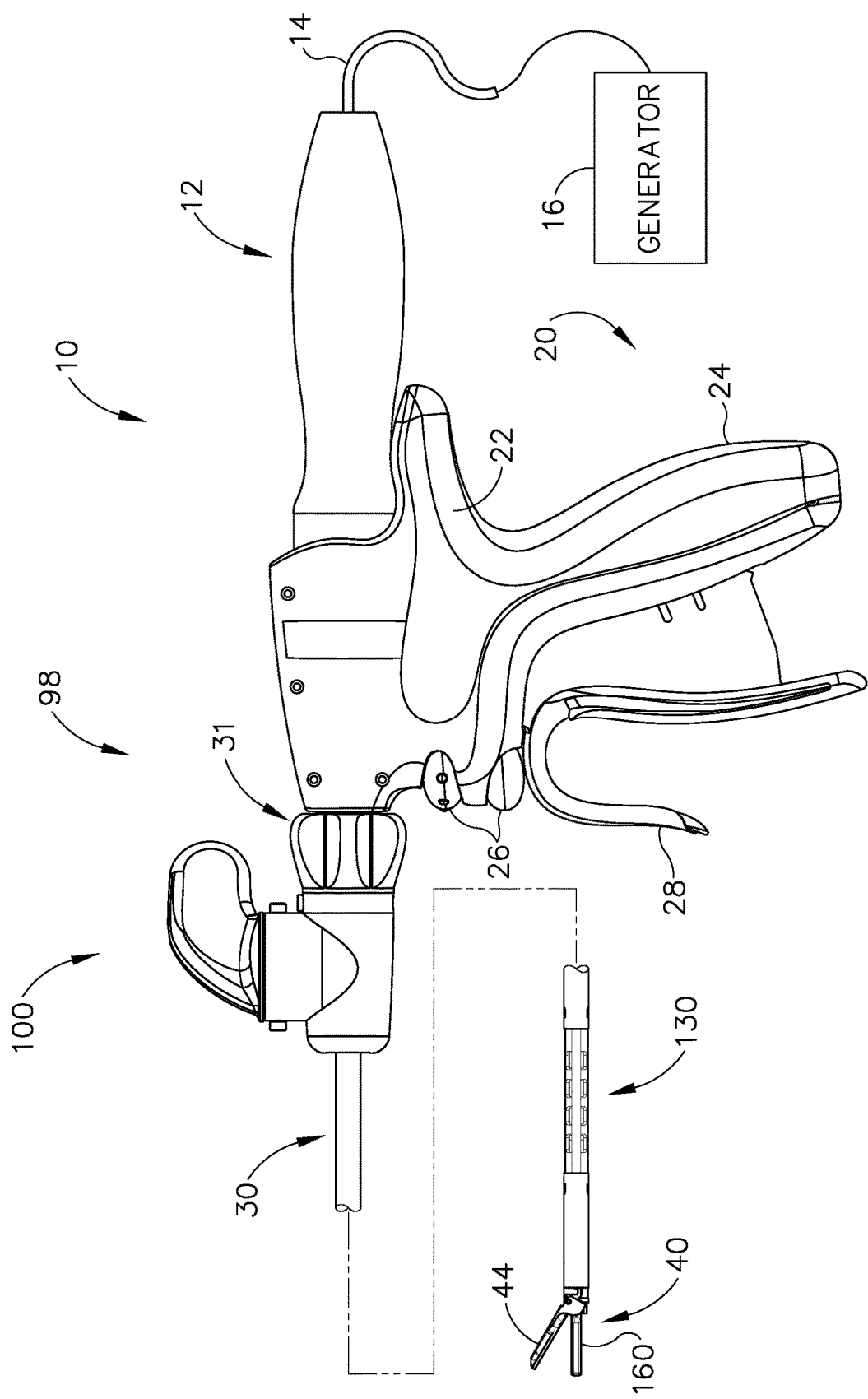
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN04, GEN11, or GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
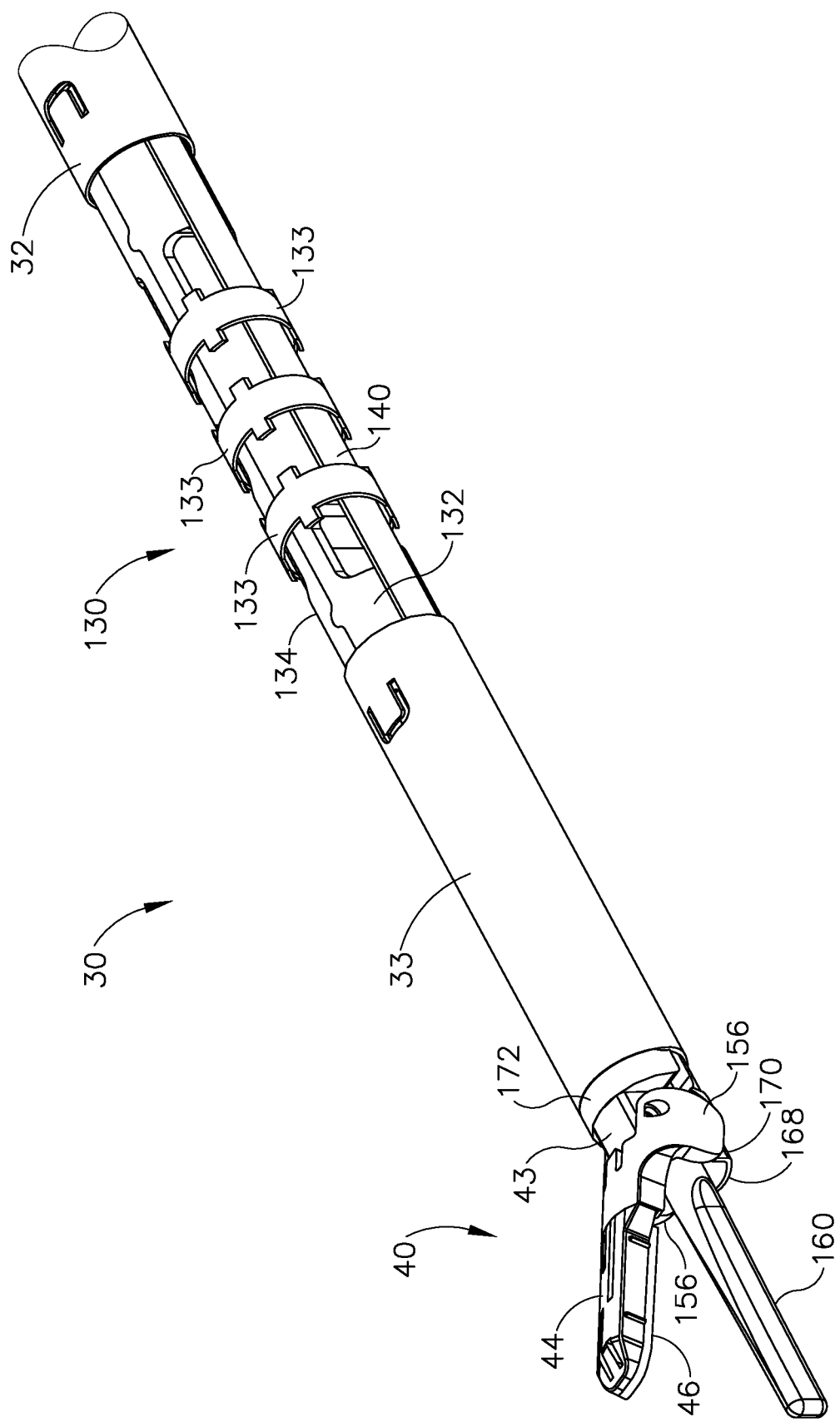
FIG. 2 depicts a perspective view of an articulation section of a shaft assembly and an end effector of the surgical instrument of FIG. 1.
Figure 3:
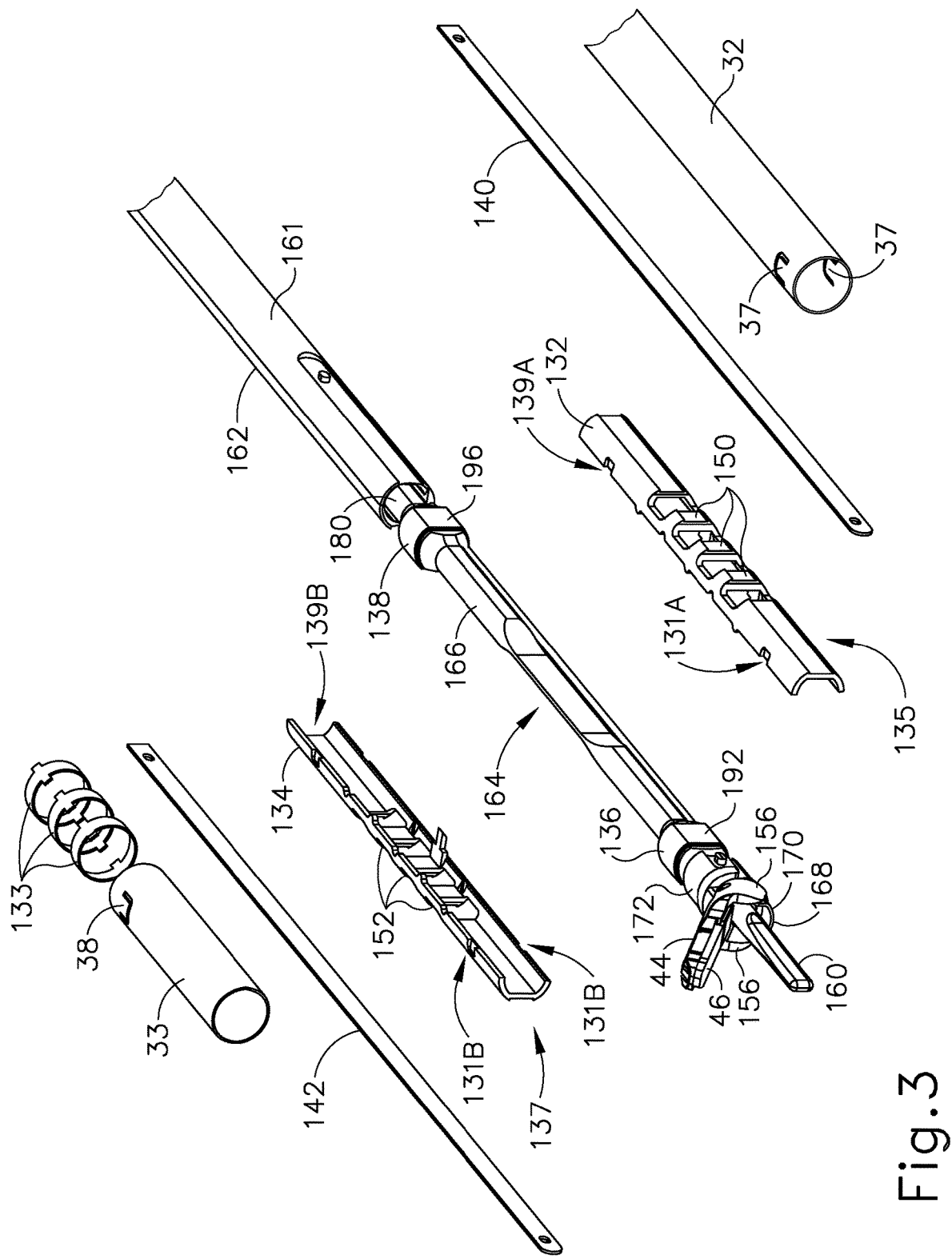
FIG. 3 depicts an exploded perspective view of the articulation section of the shaft assembly of FIG. 2.
Figure 4:
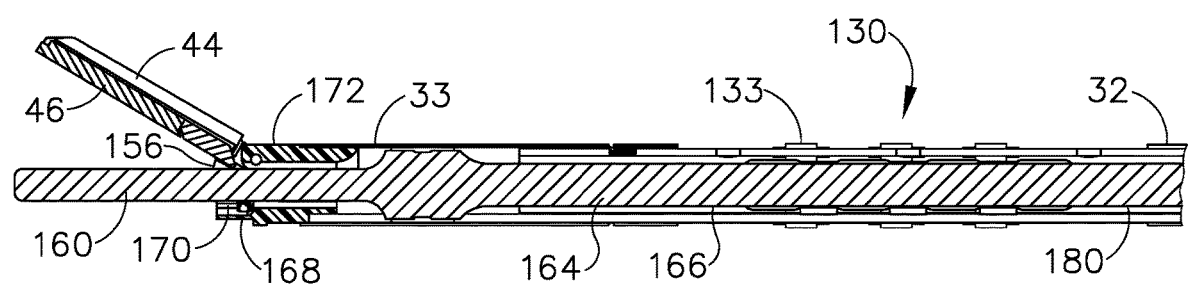
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
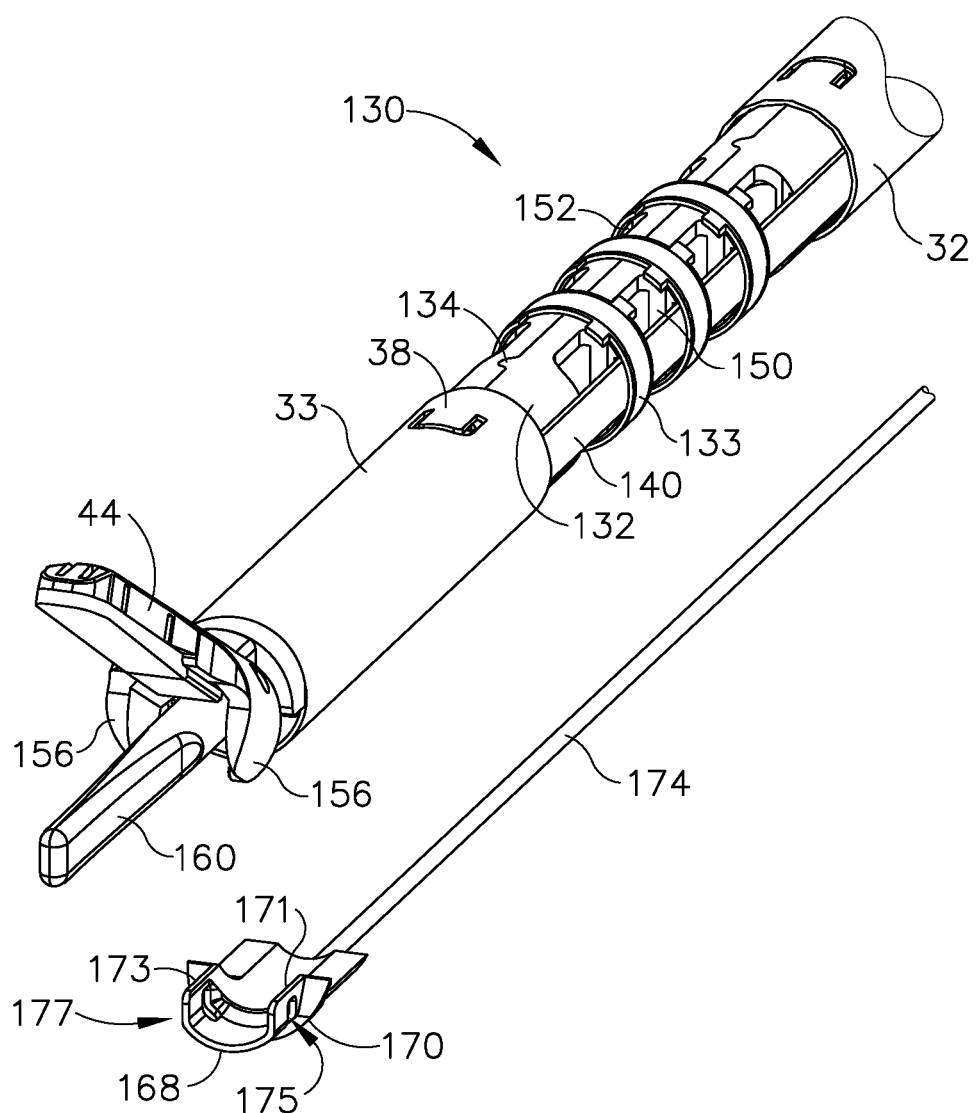
FIG. 7 depicts a partially exploded perspective view of the shaft assembly and end effector of FIG. 2.
Figure 8:
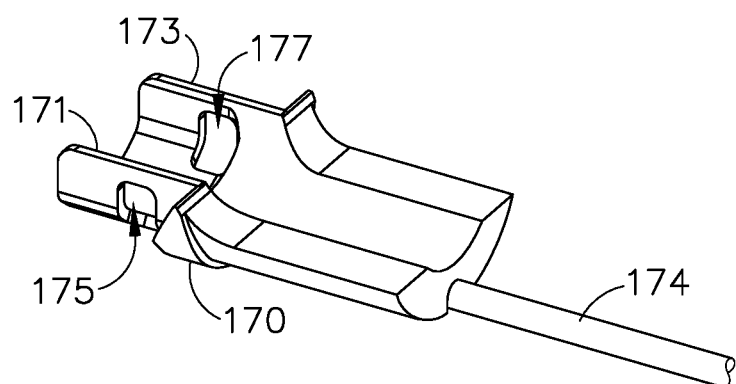
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
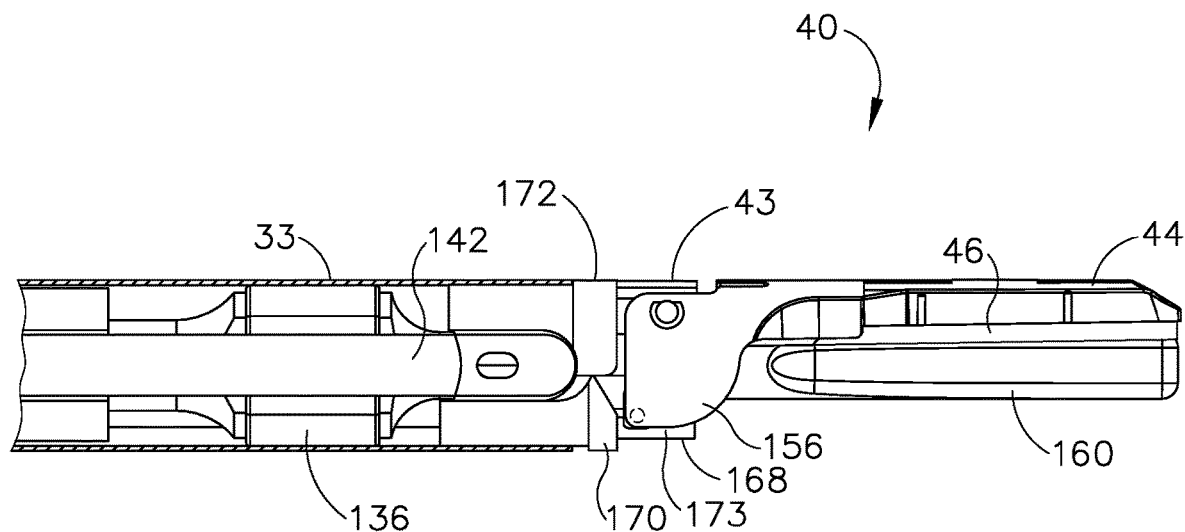
FIG. 10A depicts a side elevational view of the end effector and the distal portion of the shaft assembly of FIG. 2, with a clamp arm of the end effector in a closed position, and with an outer sheath shown in cross-section to reveal components within the outer sheath.
Figure 10B:
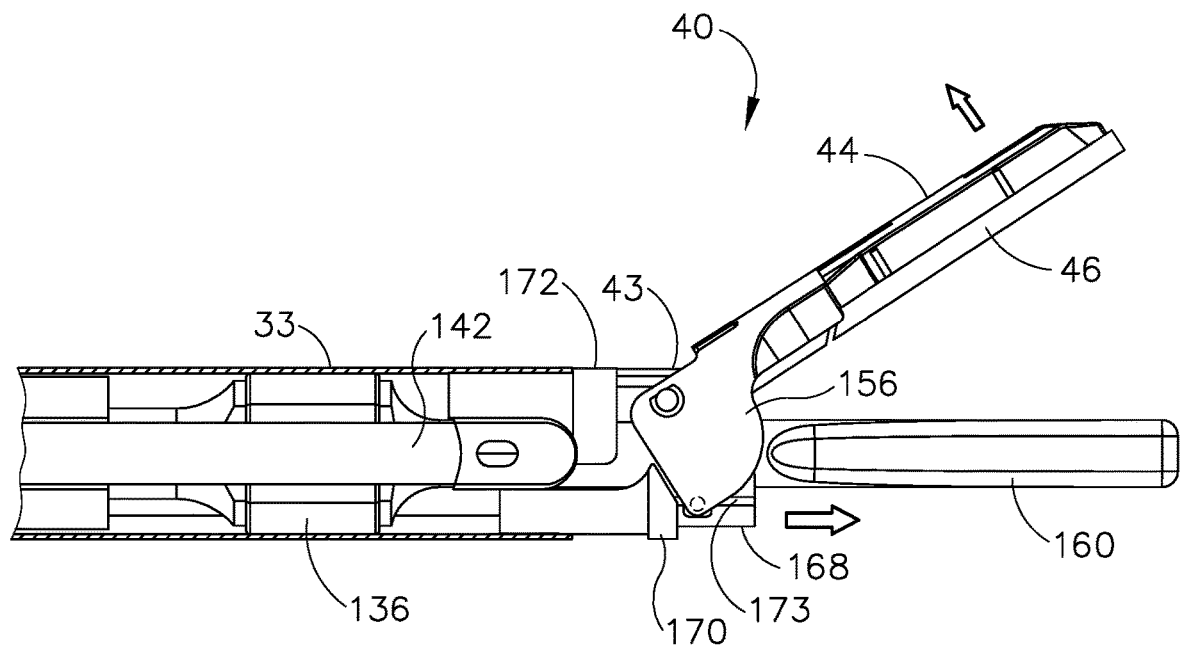
FIG. 10B depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A and 10B, longitudinal translation of cable (174) causes longitudinal translation of lower distal shaft element (170) between a proximal position (FIG. 10A) and a distal position (FIG. 10B). Longitudinal translation of lower distal shaft element (170) causes rotation of clamp arm (44) between a closed position (FIG. 10A) and an open position (FIG. 10B).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread.

In some versions, end effector (40) is operable to apply radiofrequency (RF) electrosurgical energy to tissue in addition to applying ultrasonic energy to tissue. By way of example only, end effector (40) may be configured and operable in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein.

Other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701 issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
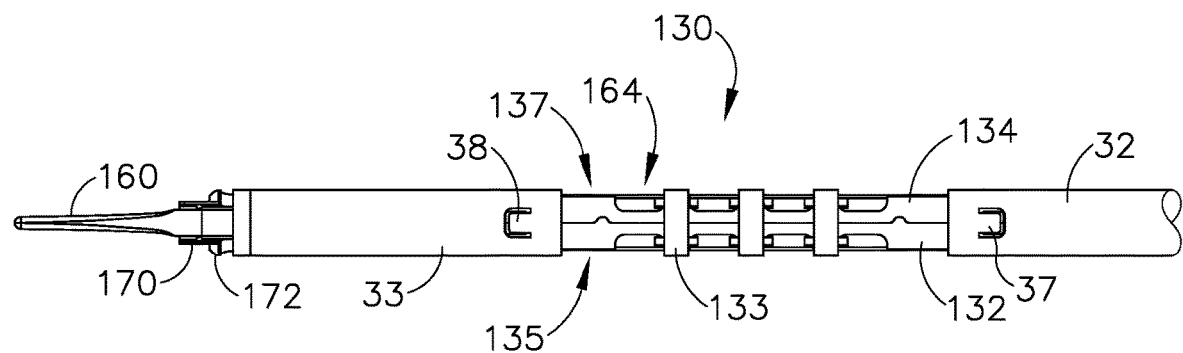
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
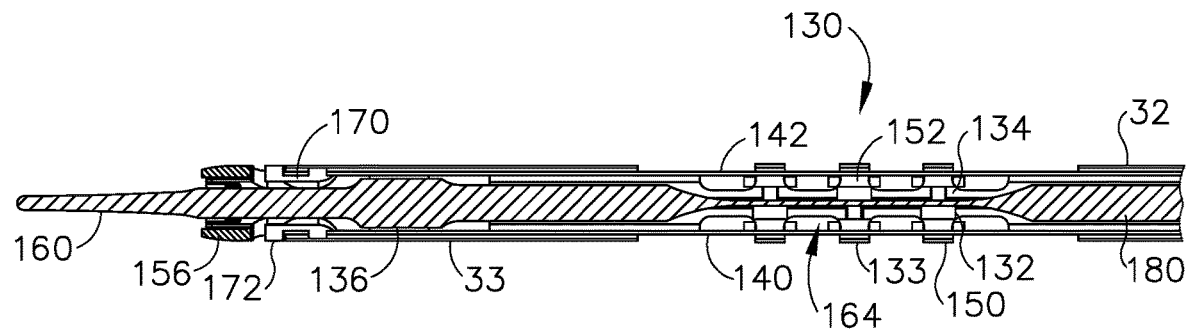
FIG. 6A depicts a cross-sectional top view of the shaft assembly and end effector of FIG. 2 in a straight configuration.
Figure 6B:
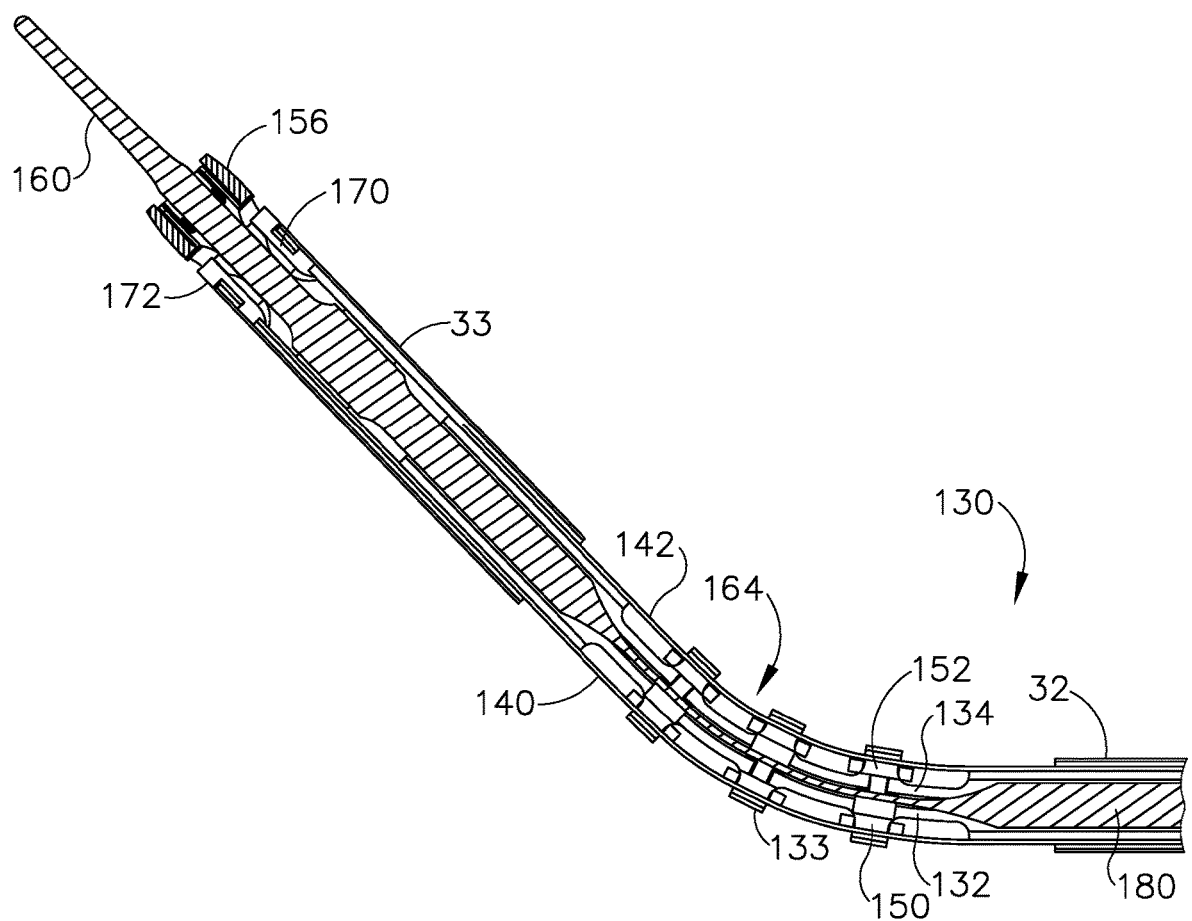
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130)

to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32); while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," filed Apr. 23, 2013, issued as U.S. Pat. No. 10,238,416 on Mar. 16, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

As best seen in FIG. 9, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112).

With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In addition to or in lieu of the foregoing, articulation section (130) and/or articulation control assembly (100) may be constructed and/or operable in accordance with at least some of the teachings of U.S. patent application Ser. No. 14/688,458, entitled "Ultrasonic Surgical Instrument with Rigidizing Articulation Drive Members," filed on Apr. 16, 2015, issued as U.S. Pat. No. 10,034,683 on Jul. 31, 2018. Alternatively, articulation section (130) and/or articulation control assembly (100) may be constructed and/or operable in any other suitable fashion.

II. Exemplary Alternative Shaft Assemblies

In some versions of instrument (10) it may be desirable to provide features that are configured to selectively provide rigidity to articulation section (130). For instance, because of various factors such as manufacturing tolerances, design limitations, material limitations, and/or other factors, some versions of articulation section (130) may be susceptible to some "play" or other small movement of the articulation section despite being relatively fixed in a given position, such that articulation section (130) is not entirely rigid. It may be desirable to reduce or eliminate such play in articulation section (130), particularly when articulation section (130) is in a straight, non-articulated configuration. Features may thus be provided to selectively rigidize articulation section (130). Various examples of features that are configured to selectively provide rigidity to articulation section (130) and/or to limit or prevent inadvertent deflection of end effector (40) will be described in greater detail below. Other examples will be apparent to those of ordinary skill in the art according to the teachings herein. It should be understood that the examples of shaft assemblies and/or articulation sections described below may function substantially similar to shaft assembly (30) discussed above.

It should also be understood that articulation section (130) may still be at least somewhat rigid before being modified to include the features described below, such that the features described below actually just increase the rigidity of articulation section (130) rather than introducing rigidity to an otherwise non-rigid articulation section (130). For instance, an articulation section (130) in the absence of features as described below may be rigid enough to substantially maintain a straight or articulated configuration; yet may still provide "play" of about 1 mm or a fraction thereof such that the already existing rigidity of articulation section (130) may be increased. Thus, terms such as "provide rigidity" and "providing rigidity" shall be understood to include just increasing rigidity that is already present in some degree. The terms "provide rigidity" and "providing rigidity" should not be read as necessarily requiring articulation section (130) to completely lack rigidity before the rigidity is "provided."

A. Exemplary Restricting Member

Figure 11:
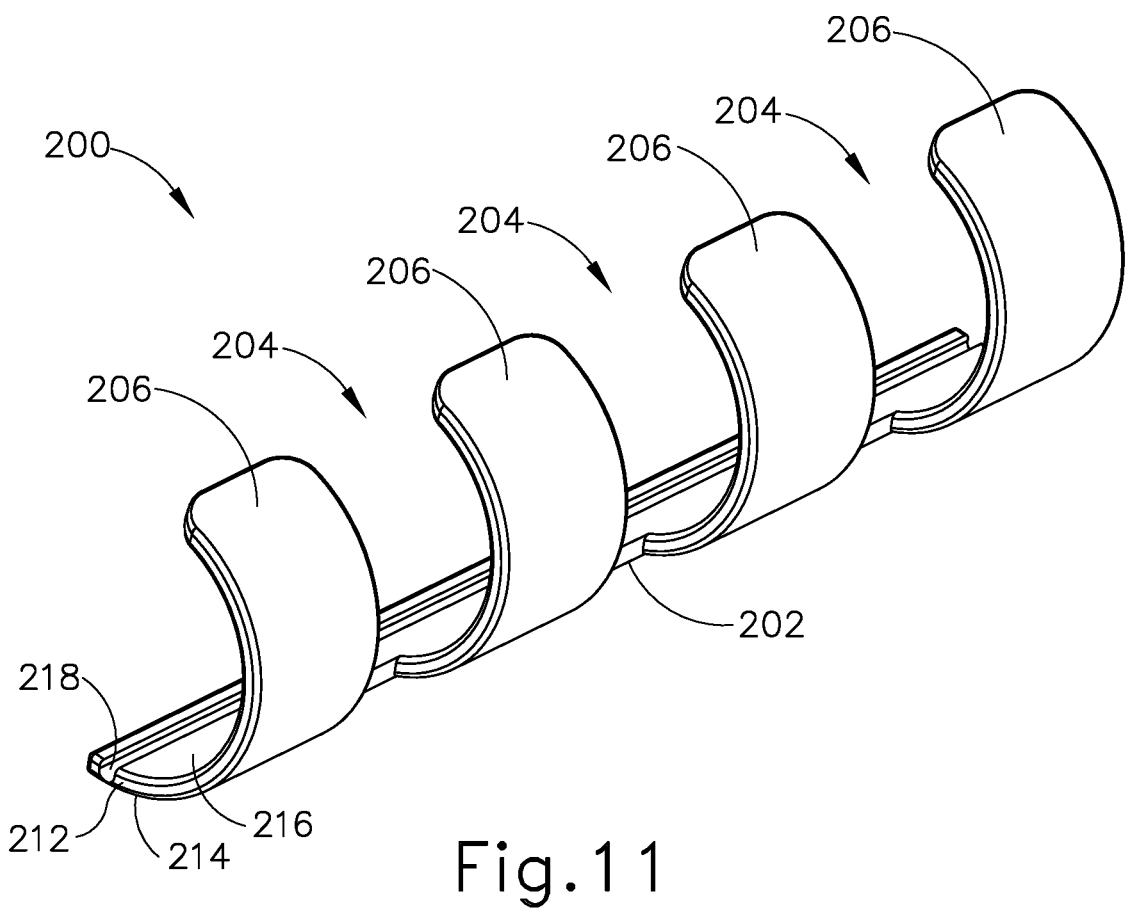
FIG. 11 depicts a perspective view of a restricting member for attaching to the articulation section of FIG. 2.
Figure 13:
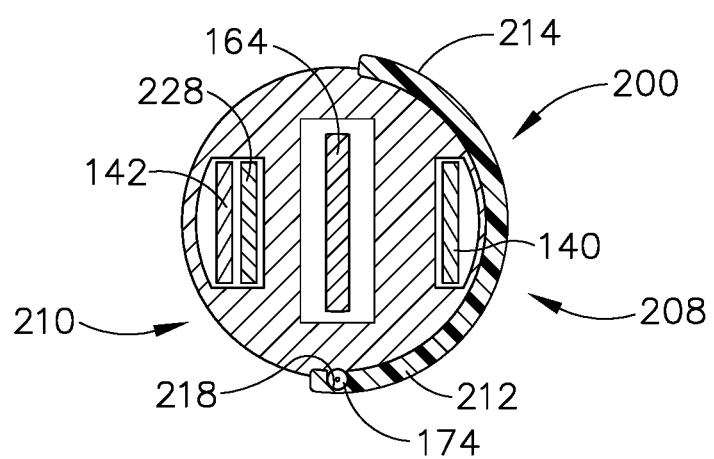
FIG. 13 depicts a cross-sectional view of the restricting member of FIG. 11 taken along line 13-13 of FIG. 12.

FIGS. 11-17 show an exemplary restricting member (200). As will be described in more detail below, restricting member (200) may function to selectively provide rigidity to one side of articulation section (130) and/or to prevent inadvertent deflection of end effector (40) relative to the longitudinal axis of shaft assembly (30). As best seen in FIGS. 11 and 13, restricting member (200) of the present example comprises a semi-circular cylindrical body (202). A plurality of slots (204) formed in opposing side surfaces of cylindrical body (202) separate a plurality of tabs (206). As shown in FIGS. 12-17, restricting member (200) is configured to be positioned about shaft assembly (30), and in particular about one side of articulation section (130). For example, as shown in FIG. 13, restricting member (200) is configured to be positioned about a first side (208) of shaft assembly (30), whereby first side (208) is generally opposite a second side (210) of shaft assembly (30). In the present example, first side (208) and second side (210) extend along the length of articulation section (130).

Figure 16A:
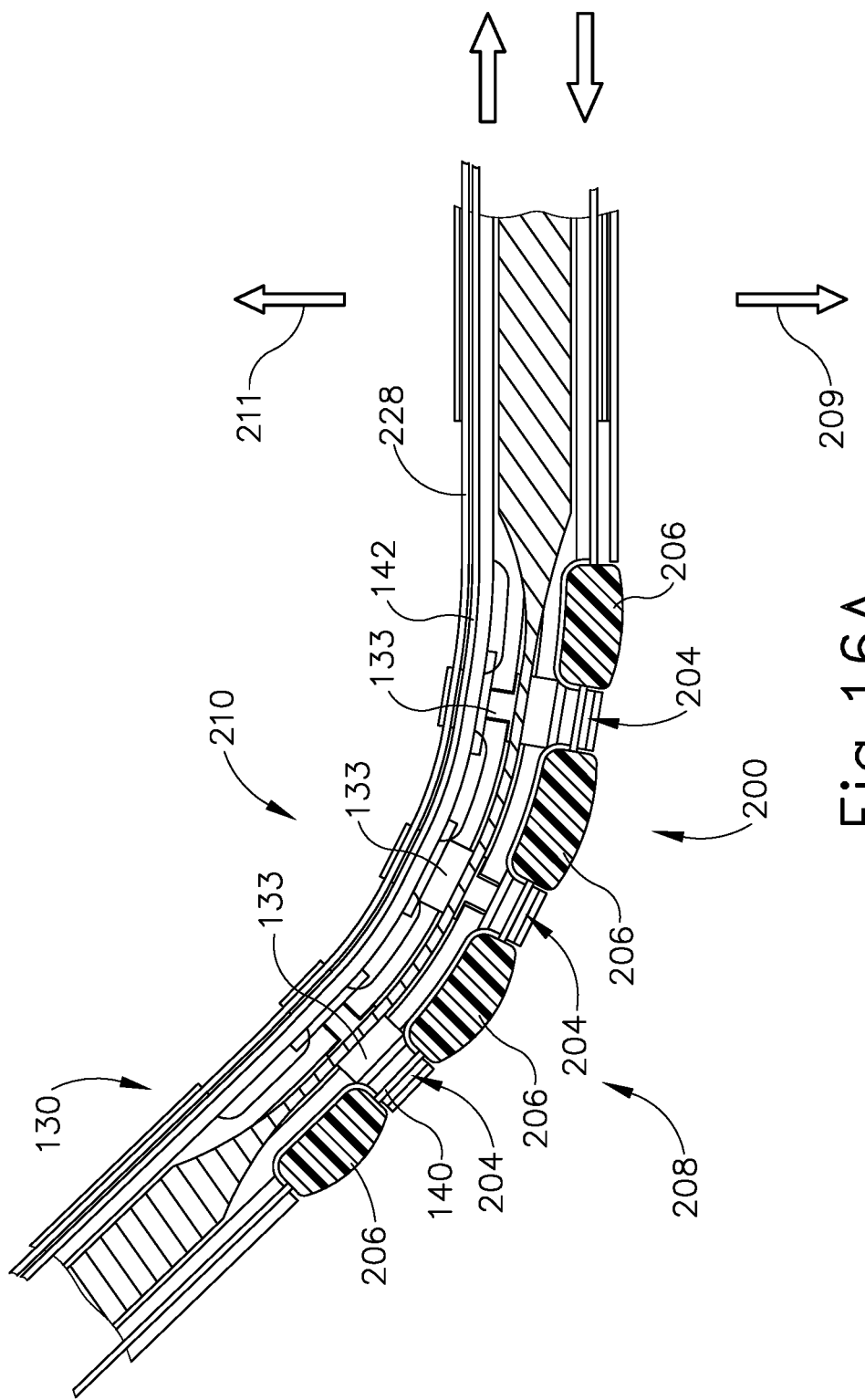
FIG. 16A depicts a cross-sectional top view of the restricting member and articulation section of FIG. 12 in an articulated configuration.

As shown in FIGS. 16A and 16B, articulation section (130) is prevented from flexing in a first direction (209) beyond a generally straight configuration (FIG. 16B) when restricting member (200) is engaged with articulation section (130). Conversely, articulation section (130) may selectively flex or articulate in a second direction (211) from the generally straight configuration shown in FIG. 16B to an articulated configuration shown in FIG. 16A, despite the presence of restricting member (200). From the articulated configuration, articulation section (130) may flex in the first direction (209) back to the generally straight configuration. As shown in FIG. 16A, articulation section (130) is operable to flex in a second direction (211) and thereby deflect end effector (40) from the longitudinal axis of shaft assembly (30) toward second side (210). As shown in FIG. 16B, articulation section (130) is also operable to return to the generally straight configuration from the articulated configuration shown in FIG. 16A.

Figure 12:
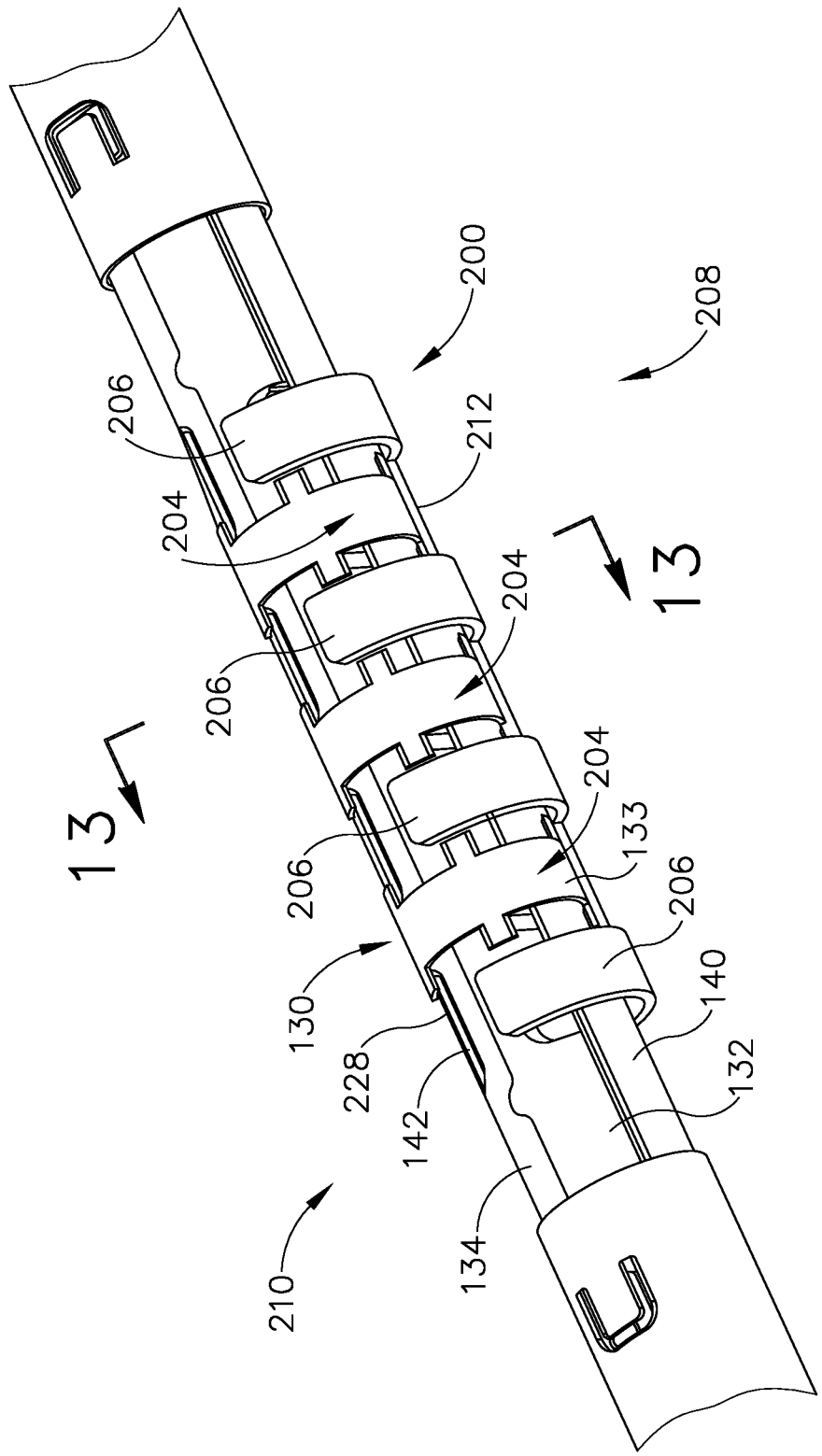
FIG. 12 depicts a perspective view of the restricting member of FIG. 11 attached to the articulation section of FIG. 2.

As shown in FIGS. 11-13, tabs (206) extend from a base (212) of body (202) of restricting member (200). Base (212) is an elongated structure for supporting tabs (206) and includes an outer surface (214) and an inner surface (216) and defines a channel (218). Tabs (206) are configured to fit snugly against or clip onto a portion of articulation section (130) and thereby remain secured to articulation section (130). As discussed above and shown in FIG. 8, cable (174) is operable to translate longitudinally relative to articulation section (130) of shaft assembly (30) to selectively pivot clamp arm (44) toward and away from blade (160). As shown in FIG. 13, channel (218) is sized to receive features associated with the bottom of articulation section (130) and cable (174) therein and acts to hold restricting member (200) to articulation section (130). Channel (218) is configured to engage articulation section (130) without restricting the longitudinal movement of cable (174) and thereby allow cable (174) to continue to slide longitudinally and actuate clamp arm (44). In other words, channel (218) is configured to allow cable (174) to translate freely relative to restricting member (200). In some versions, articulation section (130) includes a sheath or encasement around cable (174), with cable (174) being slidably disposed in the sheath. In some such versions, channel (218) is sized and configured to snugly fit and clip against the sheath.

As shown in FIG. 12, spaces defined between consecutive retention collars (133) provide clearance, allowing articulation section (130) to flex to thereby deflect end effector (40) toward the first side (208) in the first direction (209) or the second side (210) in the second direction (211). As shown in FIGS. 12, 14, and 16, with restricting member (200) positioned about articulation section (130), tabs (206) are positioned such that each tab (206) is positioned within the space defined by consecutive retention collars (133). Tabs (206) abut consecutive retention collars (133) in this state. Because tabs (206) abut consecutive retention collars (133), tabs (206) cooperate with retention collars (133) to prevent articulation section (130) from flexing in the first direction (209) beyond the straight configuration (FIG. 16B). Tabs (206) and retention collars (133) cooperate to prevent deflection of end effector (40) relative to the longitudinal axis of shaft assembly (30) by preventing movement of retention collars (133) toward one another. It should be understood that restricting member (200) may be formed of a resilient material such that restricting member (200) may be removably secured to articulation section (130) through a snap fit or a press fit. Alternatively, restricting member (200) may be removably secured to articulation section (130) in any other suitable fashion.

Restricting member (200) is sized, shaped, and configured to attach to one side of articulation section (130). By way of example and as shown in FIG. 16A, restricting member (200) is selectively attached to the first side (208) of articulation section (130). Restricting member (200) thus prevents the articulation section (130) from flexing beyond the straight configuration (FIG. 16B) toward the first side (208), as tabs (206) abut the rings or retention collars (133). This abutment prevents collars (133) from compressing toward one another to thereby flex articulation section (130) beyond the straight configuration (FIG. 16B) in the first direction (209) of first side (208). Conversely, restricting member (200) does not prevent articulation section (130) from flexing toward the second side (210) and in the second direction (211) and thereby deflect end effector (40) from the longitudinal axis of shaft assembly (30) toward the second side (210) and in the second direction (211).

It follows that an operator wishing to deflect end effector (40) in a different lateral direction may simply rotate knob (31) to rotate the entire shaft assembly (30), including articulation section (130) and end effector (40), about the longitudinal axis of shaft assembly (30). By moving the angular orientation of articulation section (130) and end effector (40) about the longitudinal axis of shaft assembly (30), the operator may deflect end effector (40) in various lateral directions from the longitudinal axis of shaft assembly (30).

While tabs (206) of restricting member (200) are shown in FIGS. 11-16B as generally straight non-angled elements, restricting member (200) may employ tabs (206) having various other cross-sectional profiles or shapes. For example, as shown in FIG. 17, a tab (206A) may include a wedge portion (220) comprising a wedge-shaped or dovetail-shaped cross-sectional profile. Wedge portion (220) of tab (206A) includes a pair of angled sidewalls (222) configured to engage a correspondingly angled pair of sidewalls (224) of a wedge portion (226) of a collar (133A). Wedge portion (226) of collar (133A) comprises a wedge-shaped cross-sectional profile that acts with adjacent collars (133A) to define a complementary space for receiving wedge portion (220) of tabs (206A). Wedge portion (220) of tabs (206A) interlock with wedge portion (226) of collars (133A) to provide a locking fit between the two elements. Inasmuch as the flexing of the articulation section (130) increases the distance between each consecutive collar (133A), the locking fit acts to firmly hold restricting member (200) onto articulation section (130) throughout the range of flexing.

B. Exemplary Dual Articulation Bands

As best seen in FIGS. 2-6B articulation section (130) includes articulation bands (140, 142) extending along respective channels (135, 137) defined between interior surfaces of retention collars (133) and exterior surfaces of ribbed body portions (132, 134). FIGS. 12-17 show a modified version of shaft assembly (30) of instrument (10) described above having dual articulation bands (142, 228) on the second side (210). The pair of overlapping articulation bands (142, 228) on second side (210) comprises the previously described articulation band (142) along with a secondary articulation band (228).

Articulation band (140) may be advanced distally while articulation bands (142, 228) are simultaneously retracted proximally in order to deflect end effector (40) from the longitudinal axis of shaft assembly (30) as shown in FIG. 16A. In order to return end effector (40) to a straight position, where end effector (40) is aligned with the longitudinal axis of shaft assembly (30) as shown in FIG. 16B, articulation band (140) may be retracted proximally while articulation bands (142, 228) are simultaneously advanced distally. In order to further rigidize articulation section (130) with end effector (40) in the straight position, articulation band (142) and secondary articulation band (228) are urged further distally to force retention collars (133) into binding engagement with tabs (206) of restricting member (200). This binding engagement provides rigidity to articulation section (130) and acts to reinforce second side (210) and neutralize or counteract the stress applied to the first side (208) by restricting member (200) when restricting member (200) is applied to first side (208). Thus, secondary articulation band (228) and articulation band (142) cooperate to provide rigidity and stabilize second side (210) of articulation section (130) and/or to prevent inadvertent deflection of end effector (40) relative to outer sheath (32). Further, when urged distally, secondary articulation band (228) and articulation band (142) counterbalance the force or stress applied to the articulation section (130) in the direction of second side (210) by restricting member (200), acting to exert force in the opposite direction to straighten articulation section (130) towards first side (208).

It should be understood that end effector (40) may already be in the straight position (i.e., aligned with the longitudinal axis of shaft assembly (30)) before articulation bands (142, 228) are urged further distally to rigidize articulation section (130); and that the further distal urging of articulation bands (142, 228) to rigidize articulation section (130) will not necessarily cause deflection of end effector (40) from the longitudinal axis of shaft assembly (30). In other words, end effector (40) may remain aligned with the longitudinal axis of shaft assembly (30) when articulation bands (142, 228) are urged further distally to rigidize articulation section (130).

While two bands (142, 228) are provided on the side opposite of restricting member (200) in this example, some other versions may simply use one band (142) on the opposite side of restricting member (200). A single band (142) may suffice to provide the binding engagement between articulation section (130) and restricting member (200) to effectively rigidize articulation section (130). However, having two bands (142, 228) instead of just one band (142, 228) may provide increased column strength along articulation section (130) by minimizing the risk of buckling that might otherwise occur if a single band (142) were urged distally to rigidize articulation section (130).

It should be understood from the foregoing that restricting member (200) and bands (142, 228) cooperate to provide rigidization or stabilization of end effector (40) for more stable operation on tissues when articulation section (130) is in a straight configuration, while still allowing articulation section (130) to flex into an articulated position on one side of shaft assembly (30). Such rigidization includes removing any "play" or other small movement that might otherwise be provided by articulation section (130) due to manufacturing tolerances and/or looseness between parts. In other words, operators who are accustomed to using non-articulating ultrasonic surgical instruments my not notice any differences in performance when articulation section (130) is in the straight configuration.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body assembly; (b) a shaft assembly, wherein the shaft assembly extends distally from the body assembly, wherein the shaft assembly defines a longitudinal axis, wherein the shaft assembly includes a waveguide; (c) an end effector, wherein the end effector is located at a distal end of the shaft assembly, wherein the end effector includes an ultrasonic blade in acoustic communication with the waveguide; (d) an articulation section having a first side and a second side, wherein the articulation section is coupled with the shaft assembly, wherein the articulation section is operable to deflect the end effector from the longitudinal axis toward the first side; and (e) a restricting member, wherein the restricting member is operable to restrict deflection of the end effector from the longitudinal axis toward the second side.

Example 2

The apparatus of Example 1, wherein the restricting member comprises a tab extending from a base, and wherein tab is disposed within a space defined by the articulation section.

Example 3

The apparatus of Example 2, wherein the space is defined at least in part by a first retention collar and a second retention collar.

Example 4

The apparatus of Example 3, wherein the tab has a wedge-shaped cross-sectional profile and the space has a complementary wedge-shaped profile.

Example 5

The apparatus of any one or more of Examples 1 through 4, further comprising an actuator extending through the articulation section from the shaft assembly to the end effector, wherein the end effector further comprises a clamp arm operable to move relative to the ultrasonic blade, wherein the actuator is movable relative to the articulation section to thereby move the clamp arm relative to the ultrasonic blade, wherein the restricting member is configured to receive a portion of the actuator.

Example 6

The apparatus of Example 5, wherein the actuator comprises a translatable member, wherein the restricting member comprises a channel defined by the base, wherein the channel is and configured to receive the translatable member therein.

Example 7

The apparatus of Example 6, wherein the translatable member comprises a cable.

Example 8

The apparatus of any one or more of Examples 1 through 7, wherein the restricting member is formed of a resilient material.

Example 9

The apparatus of any one or more of Examples 1 through 8, wherein the articulation section comprises a pair of overlapping articulation bands.

Example 10

The apparatus of Example 9, wherein the pair of overlapping articulation bands and the restricting member are disposed on opposite sides of the articulation section.

Example 11

The apparatus of any one or more of Examples 9 through 10, wherein the pair of overlapping articulation bands are configured to drive a portion of the articulation section into engagement with the restricting member to thereby rigidize the articulation section.

Example 12

The apparatus of Example 11, wherein the pair of overlapping articulation bands are configured to translate in a first direction to thereby deflect the end effector in a first lateral direction away from the longitudinal axis of the shaft assembly, wherein the pair of overlapping articulation bands are configured to translate in a second direction to thereby drive the portion of the articulation section into engagement with the restricting member to thereby rigidize the articulation section with the end effector being aligned with the longitudinal axis of the shaft assembly.

Example 13

The apparatus of any one or more of Examples 9 through 12, further comprising a third articulation band, wherein the third articulation band is configured to translate in an opposing longitudinal direction relative to the pair of overlapping articulation bands, wherein the third articulation band and the pair of overlapping articulation bands are configured to cooperate to actuate the articulation section to thereby move the end effector laterally relative to the longitudinal axis of the shaft assembly.

Example 14

The apparatus of any one or more of Examples 1 through 13, wherein the articulation section comprises a first ribbed body portion and a second ribbed body portion, and wherein the restricting member is operable to selectively engage one of the first ribbed body portion and the second ribbed body portion and to thereby rigidize the selected one of the first ribbed body portion and the second ribbed body portion.

Example 15

The apparatus of any one or more of Examples 1 through 14, wherein the articulation section comprises a plurality of recesses, and wherein the restricting member comprises a plurality of fingers oriented to be received within corresponding recesses of the plurality of recesses.

Example 16

The apparatus of Example 15, wherein the articulation section comprises a plurality of collars interlaced with the plurality of recesses.

Example 17

An apparatus comprising: (a) a body assembly; (b) a shaft assembly, wherein the shaft assembly extends distally from the body assembly, wherein the shaft assembly defines a longitudinal axis; (c) an end effector; (d) an articulation section having a first lateral side and a second lateral side, wherein the articulation section is coupled with the shaft assembly, wherein the articulation section is operable to deflect the end effector from the longitudinal axis toward the first side; (e) a restricting member coupled with the articulation section, wherein the restricting member is configured to enable deflection of the end effector from the longitudinal axis toward the first side, wherein the restricting member is further configured to prevent deflection of the end effector from the longitudinal axis toward the second side; and (f) a translating member, wherein the translating member is translatable in a first direction to deflect the end effector from the longitudinal axis toward the first side, wherein the translating member is translatable in a second direction to bind a portion of the restricting member against a portion of the articulation section to thereby rigidize the articulation section while the end effector is aligned with the longitudinal axis.

Example 18

The apparatus of Example 17, wherein the restricting member comprises a plurality of fingers extending from a body, and wherein each finger is disposed within a space defined by the articulation section, wherein the translating member is operable to bind portions of the articulation section against the fingers of the restricting member to thereby rigidize the articulation section while the end effector is aligned with the longitudinal axis.

Example 19

The apparatus of Example 18, wherein the plurality of fingers and the body are configured to clip onto the articulation section.

Example 20

A method of operating an apparatus, wherein the apparatus comprises: (a) a shaft assembly defining a longitudinal axis; (b) an end effector; (c) an articulation section, wherein the articulation section is operable to deflect the end effector laterally from the longitudinal axis, wherein the articulation section comprises a binding feature; (d) a restricting member coupled with the articulation section, wherein the restricting member is configured to enable deflection of the end effector from the longitudinal axis in a first direction of deflection, wherein the restricting member is further configured to prevent deflection of the end effector from the longitudinal axis in a second direction of deflection, wherein the restricting member comprises a binding feature associated with the binding feature of the articulation section; and (e) a translating member operable to actuate the articulation section; wherein the method comprises: (a) driving the translating member in a first longitudinal direction to deflect the end effector from the longitudinal axis in the first direction of deflection, thereby positioning the end effector in a deflected position; (b) driving the translating member in a second longitudinal direction to move the end effector in the second direction of deflection back toward the longitudinal axis, thereby positioning the end effector in a straight position; and (c) urging the translating member further in the second longitudinal direction to provide binding engagement between the binding feature of the restricting member and the binding feature of the articulation section, thereby rigidizing the articulation section with the end effector in the straight position.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus comprising:
   (a) a body assembly;
   (b) a shaft assembly that extends distally from the body assembly, wherein the shaft assembly defines a longitudinal axis;
   (c) an end effector located at a distal end of the shaft assembly;
   (d) an articulation section having a first side and a second side, wherein the articulation section is coupled with the shaft assembly, wherein the articulation section is operable to deflect the end effector from the longitudinal axis toward the first side, wherein the articulation section comprises first and second translatable members that are disposed on the first side of the articulation section;
   (e) a restricting member operable to restrict deflection of the end effector from the longitudinal axis toward the second side; and
   (f) an actuator configured to selectively articulate the articulation section thereby deflecting the end effector from the longitudinal axis.

2. The apparatus of claim 1, wherein the actuator extends through the articulation section from the shaft assembly to the end effector.

3. The apparatus of claim 1, wherein the actuator comprises a translatable closure member, wherein the restricting member comprises a channel extending along a length of the restricting member, wherein the channel is configured to receive the translatable closure member therein.

4. The apparatus of claim 1, wherein the actuator comprises a knob that is configured to be actuated by a user.

5. The apparatus of claim 4, wherein the knob is configured to selectively lock in a particular rotational position to enable the user to selectively lock the articulation section in a particular deflected position relative to the longitudinal axis.

6. The apparatus of claim 1, wherein the first and second translatable members include respective first and second channels, wherein the knob includes first and second pins extending from the knob, wherein the first and second pins are configured to be rotatably and slidably disposed within respective the first and second channels formed in the first and second translatable members.

7. The apparatus of claim 6, wherein the first and second channels are positioned on opposite sides of an axis of rotation of the knob, such that rotation of the knob about the axis of rotation is configured to cause opposing longitudinal translation of the first and second translatable members.

8. The apparatus of claim 1, further comprising a third translatable member, wherein rotation of the knob in a first direction causes distal longitudinal translation of the first and second translatable members and proximal longitudinal translation of the third translatable member, wherein rotation of the knob in a second direction, which is opposite the first direction, causes proximal longitudinal translation of the first translatable and second translatable members and distal longitudinal translation of the third translatable member.

9. The apparatus of claim 1, wherein the shaft assembly includes a waveguide, wherein the end effector includes an ultrasonic blade and a clamp arm operable to move relative to the ultrasonic blade, wherein the ultrasonic blade is in acoustic communication with the waveguide, wherein the actuator is movable relative to the articulation section to thereby move the clamp arm relative to the ultrasonic blade, wherein the restricting member is configured to receive a portion of the actuator.

10. The apparatus of claim 1, wherein the restricting member is operable to selectively clip on and off of the articulation section.

11. The apparatus of claim 1, wherein the restricting member is formed entirely of a resilient material.

12. The apparatus of claim 1, wherein the restricting member is integrally formed together as a unitary piece.

13. The apparatus of claim 1, wherein the first and second translating members comprise first and second articulation bands, wherein the articulation section comprises a third articulation band, wherein the third articulation band and the restricting member are disposed on the second side of the articulation section, wherein the first and second articulation bands are configured to drive a portion of the articulation section into engagement with the restricting member to thereby rigidize the articulation section.

14. The apparatus of claim 13, wherein the first and second articulation bands are configured to translate in a first direction along the longitudinal axis to thereby deflect the end effector in a first lateral direction away from the longitudinal axis of the shaft assembly, wherein the first and second articulation bands are configured to translate in a second direction along the longitudinal axis to thereby drive the portion of the articulation section into engagement with the restricting member to thereby rigidize the articulation section with the end effector being aligned with the longitudinal axis of the shaft assembly.

15. The apparatus of claim 1, wherein the first and second translatable members are configured to drive a portion of the articulation section into engagement with the restricting member to thereby rigidize the articulation section with the end effector being aligned with the longitudinal axis of the shaft assembly.

16. An apparatus comprising:
(a) a body assembly;
(b) a shaft assembly extending distally from the body assembly, wherein the shaft assembly defines a longitudinal axis, wherein the shaft assembly includes a waveguide;
(c) an end effector located at a distal end of the shaft assembly, wherein the end effector includes an ultrasonic blade in acoustic communication with the waveguide;
(d) a translatable member configured to translate along the longitudinal axis of the shaft assembly to actuate the end effector;
(e) an articulation section having a first side and a second side, wherein the articulation section is coupled with the shaft assembly, wherein the articulation section is operable to deflect the end effector from the longitudinal axis toward the first side;
(f) a restricting member operable to restrict deflection of the end effector from the longitudinal axis toward the second side, wherein the restricting member includes a channel extending longitudinally along the restricting member, wherein the channel is sized and configured to receive the translatable member; and
an actuator configured to the actuated by a user to selectively articulate the articulation section thereby deflecting the end effector from the longitudinal axis.

17. The apparatus of claim 16, wherein the actuator comprises a knob configured to selectively lock in a particular rotational position to enable the user to selectively lock the articulation section in a particular deflected position relative to the longitudinal axis.

18. The apparatus of claim 16, wherein the end effector includes a clamp arm, wherein the translatable member is configured to translate along the longitudinal axis of the shaft assembly to pivot the clamp arm relative to the ultrasonic blade, wherein the channel is sized and configured to slidably contact the translatable member.

19. The apparatus of claim 16, wherein the restricting member is disposed on the second side of the articulation section.

20. An apparatus comprising:
(a) a shaft assembly extending distally and defining a longitudinal axis;
(b) an end effector located at a distal end of the shaft assembly;
(c) an articulation section having a first side and a second side, wherein the articulation section is coupled with the shaft assembly, wherein the articulation section is operable to deflect the end effector from the longitudinal axis toward the first side;
(d) a restricting member operable to restrict deflection of the end effector from the longitudinal axis toward the second side, wherein the restricting member is operable to selectively clip on and off of the articulation section; and
(e) an actuator configured to selectively articulate the articulation section thereby deflecting the end effector from the longitudinal axis.

* * * * *